(12) United States Patent
Cao et al.

(10) Patent No.: US 11,202,360 B2
(45) Date of Patent: Dec. 14, 2021

(54) SYSTEM WITH A SPATIALLY EXPANSIVE X-RAY SOURCE FOR X-RAY IMAGING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 12 days.

(21) Appl. No.: 16/742,758

(22) Filed: Jan. 14, 2020

(65) Prior Publication Data

US 2020/0163194 A1    May 21, 2020

Related U.S. Application Data

(63) Continuation of application No. PCT/CN2017/094440, filed on Jul. 26, 2017.

(51) Int. Cl.
*A61B 6/00* (2006.01)
*H05G 1/02* (2006.01)
(Continued)

(52) U.S. Cl.
CPC ............ *H05G 1/02* (2013.01); *A61B 6/032* (2013.01); *A61B 6/10* (2013.01); *A61B 6/4007* (2013.01);
(Continued)

(58) Field of Classification Search
CPC ......... A61B 6/032; A61B 6/4007; A61B 6/10; A61B 6/4014; A61B 6/4028; A61B 6/4035; A61B 6/0487; A61B 6/4488; A61B 6/466; A61B 6/037; A61B 6/4417; A61B 6/4435; A61B 6/025; A61B 6/035; A61B 6/0492; A61B 6/4085; A61B 6/4258; A61B 6/4233; A61B 8/4416; A61B 10/0233; A61B 6/03; A61B 6/0407; H01J 2235/062; H01J 35/065; H01J 2201/30469; H01J 2235/02; H01J 35/045; H01J 35/116; H01J 2235/081; H01J 2235/168; H01J 35/08; H01J 1/3048; H01J 2235/068; H01J 2235/086; H01J 35/10; H01J 35/101; H01J 35/112;
(Continued)

(56) References Cited

U.S. PATENT DOCUMENTS

2003/0198318 A1 * 10/2003 Price ................. H01J 35/065
378/122
2005/0175151 A1   8/2005 Dunham et al.
(Continued)

FOREIGN PATENT DOCUMENTS

CN    1758877 A    4/2006
CN    1833299 A    9/2006
(Continued)

*Primary Examiner* — Irakli Kiknadze
(74) *Attorney, Agent, or Firm* — IPRO, PLLC

(57) ABSTRACT

Disclosed herein is a system, comprising: a first X-ray source comprising a plurality of X-ray generators configured to respectively emit a plurality of X-rays toward an object; and a first X-ray detector configured to detect images of the object formed respectively by the plurality of X-rays from the first X-ray source.

18 Claims, 20 Drawing Sheets

(51) Int. Cl.
*A61B 6/03* (2006.01)
*A61B 6/10* (2006.01)
*G01N 23/046* (2018.01)
*H01J 35/08* (2006.01)

(52) U.S. Cl.
CPC ......... *A61B 6/4035* (2013.01); *G01N 23/046* (2013.01); *H01J 35/08* (2013.01); *G01N 2223/204* (2013.01); *H01J 2235/081* (2013.01); *H01J 2235/168* (2013.01)

(58) Field of Classification Search
CPC .......... H01J 35/147; H01J 47/08; H01J 35/16; H01J 2235/08; H01J 35/153; H01J 35/18; H01J 35/14; H01J 35/186; H01J 2235/083; H01J 31/49; H01J 2231/50021; H01J 2231/50068; H01J 29/861; H01J 29/90; H01J 9/18; H01J 9/26; H01J 9/28; H05G 1/02; H05G 1/025; H05G 1/52; H05G 1/30; H05G 1/34; H05G 1/70; G01N 2223/204; G01N 23/046; G01N 2223/419; G01N 2223/505; G01N 2223/108; G01N 23/2255; G01N 23/04; G01N 2223/308; G01N 2223/6113; G01N 23/083; G01N 23/20075; G01N 29/2437; G01N 29/262; G01T 1/2914; G01T 1/2985; A61N 2005/1061; A61N 5/1049; G01V 5/0008; H02J 7/0042; H05K 13/0815; H05K 13/082; H05K 3/00
USPC ........................................ 378/4, 19, 98.8, 62
See application file for complete search history.

(56) References Cited

U.S. PATENT DOCUMENTS

| | | | |
|---|---|---|---|
| 2007/0235772 A1* | 10/2007 | Jin | ............................ G09G 3/22 |
| | | | 257/236 |
| 2009/0074134 A1 | 3/2009 | Jeffery | |
| 2009/0185660 A1 | 7/2009 | Zou et al. | |
| 2013/0235976 A1* | 9/2013 | Jeong | ...................... H01J 3/021 |
| | | | 378/121 |

FOREIGN PATENT DOCUMENTS

| | | |
|---|---|---|
| CN | 101494149 A | 7/2009 |
| CN | 101842052 A | 9/2010 |
| CN | 104323787 A | 2/2015 |
| WO | 2015079393 A1 | 6/2015 |

\* cited by examiner

SYSTEM WITH A SPATIALLY EXPANSIVE X-RAY SOURCE FOR X-RAY IMAGING

TECHNICAL FIELD

The disclosure herein relates to a system that has a spatially expansive X-ray source for imaging.

BACKGROUND

An X-ray computed tomography (CT) image system has been widely used in various applications such as medical imaging. The X-ray CT image system may consist of an X-ray generator and an X-ray detector. The X-ray generator may be configured to generate X-rays toward an object to be imaged. The X-ray detector may be configured to receive the X-rays after the X-ray passes through the object of interest, which can be used to generate a two-dimensional image of the object. Both the X-ray generator and the X-ray detector may rotate with an angle of 360/N, where N represents a number of scans needed to reconstruct a three-dimensional image of the object. After both the X-ray generator and the X-ray detector move to the new position, another scan of the object is performed. Accordingly, another two-dimensional image of the object can be generated. The above process repeats until all the N scans are completed to obtain N two-dimensional images of the object. Finally, the three-dimensional image of the object can be generated based on the N two-dimensional images of the objects as described herein.

SUMMARY

Disclosed herein is a system, comprising: a first X-ray source comprising a plurality of X-ray generators configured to respectively emit a plurality of X-rays toward an object; and a first X-ray detector configured to detect images of the object formed respectively by the plurality of X-rays from the first X-ray source.

According to an embodiment, the system further comprises a computer system configured to reconstruct a three-dimensional structure of the object based on the images.

According to an embodiment, the plurality of X-ray generators are configured to emit X-rays at different times.

According to an embodiment, the plurality of X-ray generators are arranged in a row or in a grid.

According to an embodiment, the grid is selected from a group consisting of a rectangular array, a hexagonal array, a pentagon array, and a honeycomb array.

According to an embodiment, the plurality of X-rays have different spatial distributions.

According to an embodiment, each of the plurality of X-ray generators comprises: a cathode in a recess of a first substrate; a counter electrode on a sidewall of the recess, configured to cause field emission of electrons from the cathode; and a metal anode configured to receive the electrons emitted from the cathode and to emit X-ray from impact by the electrons on the metal anode.

According to an embodiment, the cathode comprises a plurality of carbon nanotubes.

According to an embodiment, the counter electrode is a continuous ring or dotted ring around the sidewall.

According to an embodiment, the system further comprises a shield electrode between the counter electrode and the metal anode, the shield electrode configured to repel the electrons facing the metal anode.

According to an embodiment, the shield electrode is a continuous ring or dotted ring around the sidewall.

According to an embodiment, the first substrate comprises silicon or silicon oxide.

According to an embodiment, the metal anode comprises one or more metals selected from a group consisting of tungsten, molybdenum, rhenium, copper and combinations thereof.

According to an embodiment, the system further comprises a second substrate bonded to the first substrate, wherein the second substrate covers the recess.

According to an embodiment, the metal anode is supported by the second substrate.

According to an embodiment, the metal anode is on a side of the second substrate away from the cathode.

According to an embodiment, the cathode comprises an array of carbon nanotubes.

According to an embodiment, the system further comprises: a second X-ray source comprising a plurality of X-ray generators configured to respectively emit a plurality of X-rays toward the object; and a second X-ray detector configured to detect images of the object formed respectively by the plurality of X-rays from the second X-ray source; wherein a combination of the first X-ray source and the first X-ray detector and a combination of the second X-ray source and the second X-ray detector have different orientations.

According to an embodiment, the orientations are perpendicular to each other.

DETAILED DESCRIPTION

Figure 1:
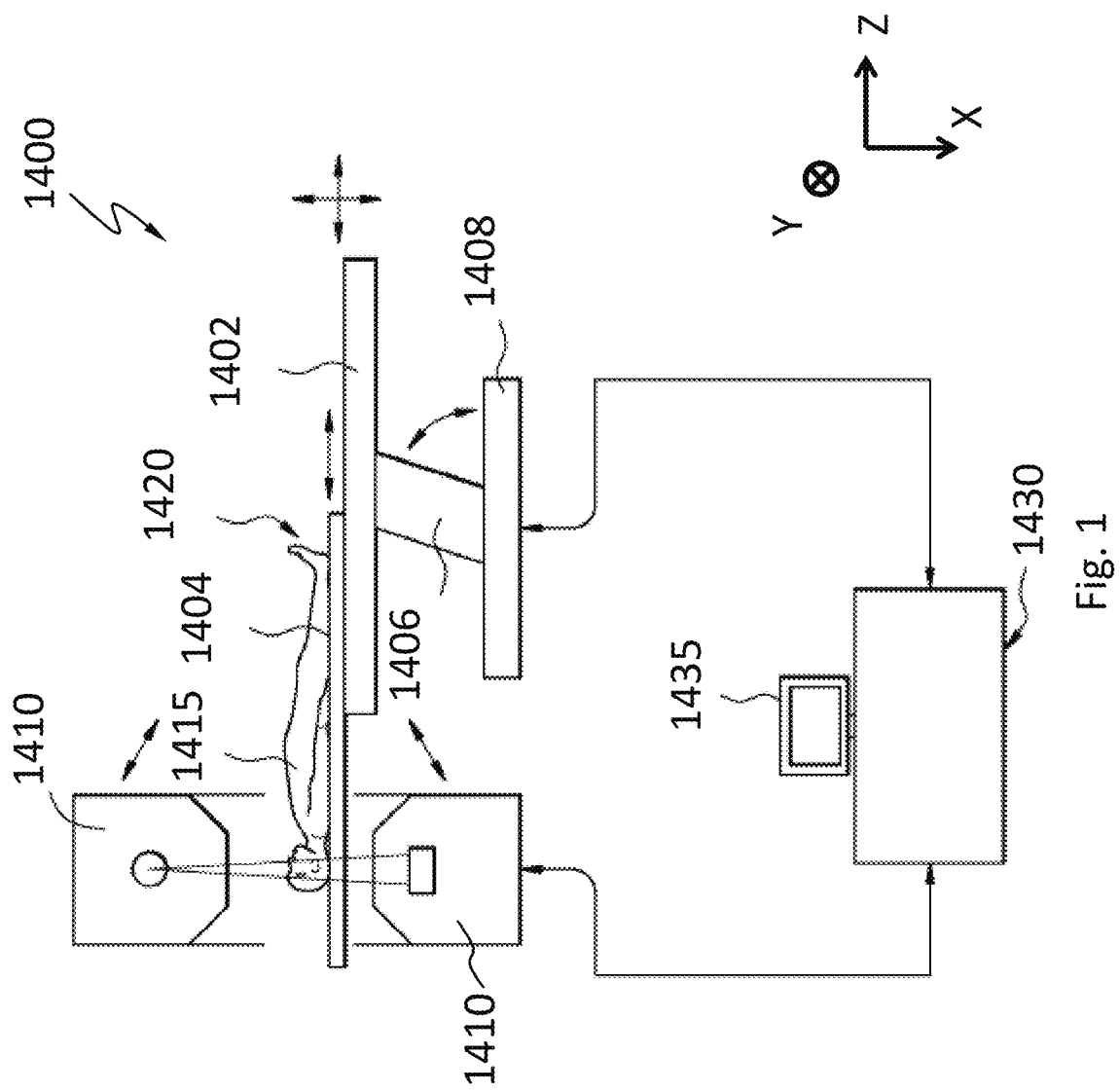
FIG. 1 schematically shows an X-ray computed tomography (CT) imaging system.

FIG. 1 schematically shows an X-ray computed tomography (CT) imaging system 1400. The X-ray CT imaging system 1400 includes a source-and-detector assembly 1410, a sample holder 1420, and an operation console 1430. The source-and-detector assembly 1410 may include an X-ray source configured to emit an X-ray toward an object 1415 (e.g., a person as shown in FIG. 1) on the sample holder 1420 (e.g., a table), and an X-ray detector configured to acquire X-ray transmitted through the object ("projection data").

The operation console 1430 may be configured to control the X-ray CT imaging system 1400. The operation console 1430 may have a computer configured to reconstruct an image (e.g., a three-dimensional image) of the object 1415 based on the projection data, and displays the image on a display 1435. In an example, the computer may generate multiple two-dimensional images based on the projection data and reconstruct a three-dimensional image based on the two-dimensional images.

The operation console 1430 may control the operations of the source-and-detector assembly 1410 and the sample holder 1420 (e.g., the table), respectively. For example, the source-and-detector assembly 1410 may be turned on or off under the control of the operator console 1430. The sample holder 1420 (e.g., the table) positions the object 1415 so that a selected region of the object 1415 will be imaged. The positioning may be achieved using an alignment mechanism to adjust the height of a tabletop 1402 and a horizontal distance by which a cradle 1404 extends into the source-and-detector assembly 1410.

The height of the tabletop 1402 may be adjusted by swinging a columnar support 1406 with the root of the columnar support at a base 1408 as a center. With the swing of the columnar support 1406, the tabletop 1402 is displaced vertically and horizontally. The cradle 1404 is moved horizontally on the tabletop 1402, whereby the horizontal displacement of the tabletop 1402 is canceled out. Under some circumstances, imaging may be performed with the source-and-detector assembly 1410 tilted.

Figure 2:
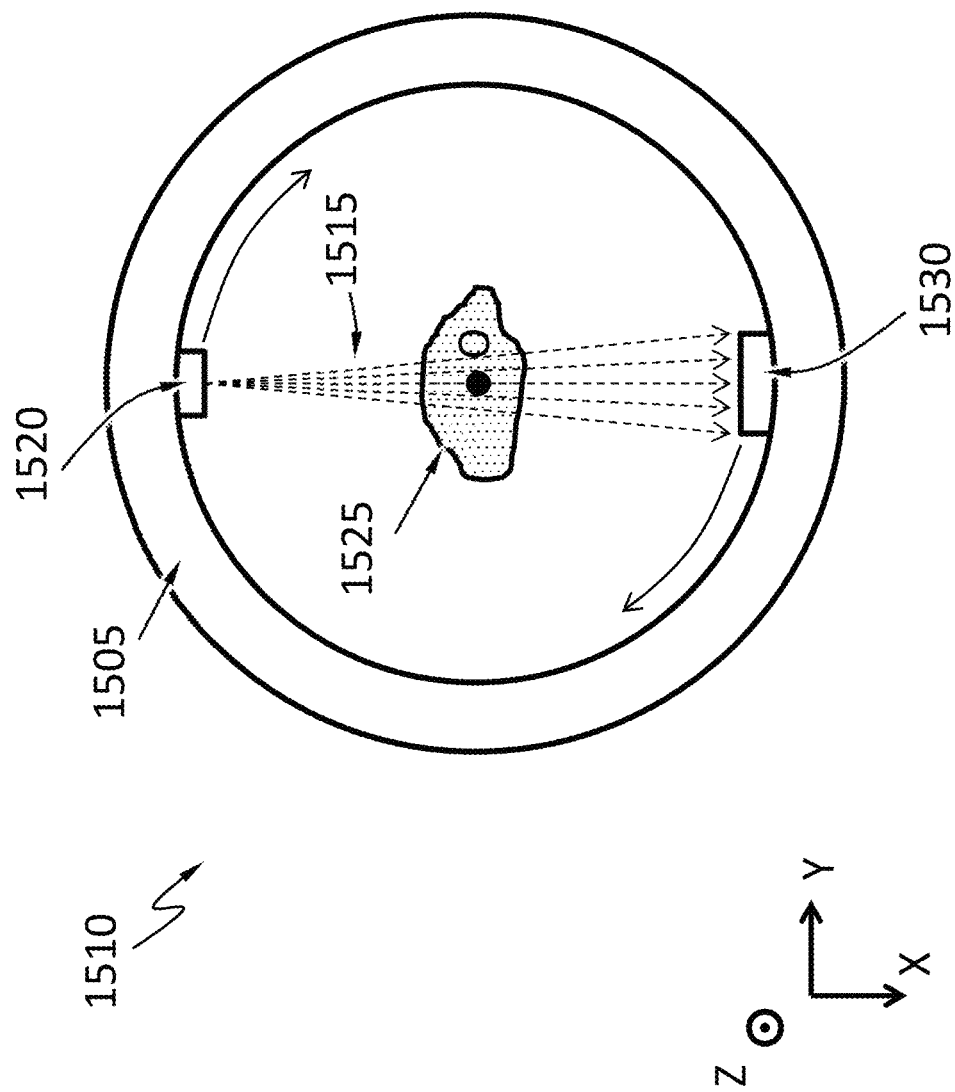
FIG. 2 schematically shows a side view of a source-and-detector assembly, which may be suitable to be used in the CT imaging system as shown in FIG. 1.

FIG. 2 schematically shows a side view of a source-and-detector assembly 1510. The source-and-detector assembly 1510 includes an X-ray source 1520, and an X-ray detector 1530. The X-ray source 1520 and the X-ray detector 1530 may be mounted to a frame 1505. For example, the X-ray source 1520 and the X-ray detector 1530 are opposite to each other so that the X-ray emitted from the X-ray source 1520 may be received by the X-ray detector 1530 after passing through the object 1525. The object 1525 may be located in the center or near the center of the frame 1505. During operation, the X-ray source 1520 may emit a plurality of X-rays 1515 (e.g., a fan beam as shown in FIG. 2) toward the object 1525. The plurality of X-rays 1515 may have different interaction with the object 1525. The X-ray source 1520 and the X-ray detector 1530 may rotate relative to the object 1525. The X-ray source 1520 and the X-ray detector 1530 may rotate independently. The X-ray source 1520 and the X-ray detector 1530 may rotate without relative movement with respect to each other. The X-ray source 1520 and the X-ray detector 1530 may rotate relative to the frame 1505. The X-ray source 1520 and the X-ray detector 1530 may rotate with the frame 1505 without movement relative to the frame 1505. The rotation of the X-ray source 1520 and the X-ray detector 1530 may be around the Z axis as shown in FIG. 2. The X-ray source 1520 and the X-ray detector 1530 may be configured to emit X-ray toward the object 1525 and detect images of the object 1525, respectively, at any rotational location.

Figure 3:
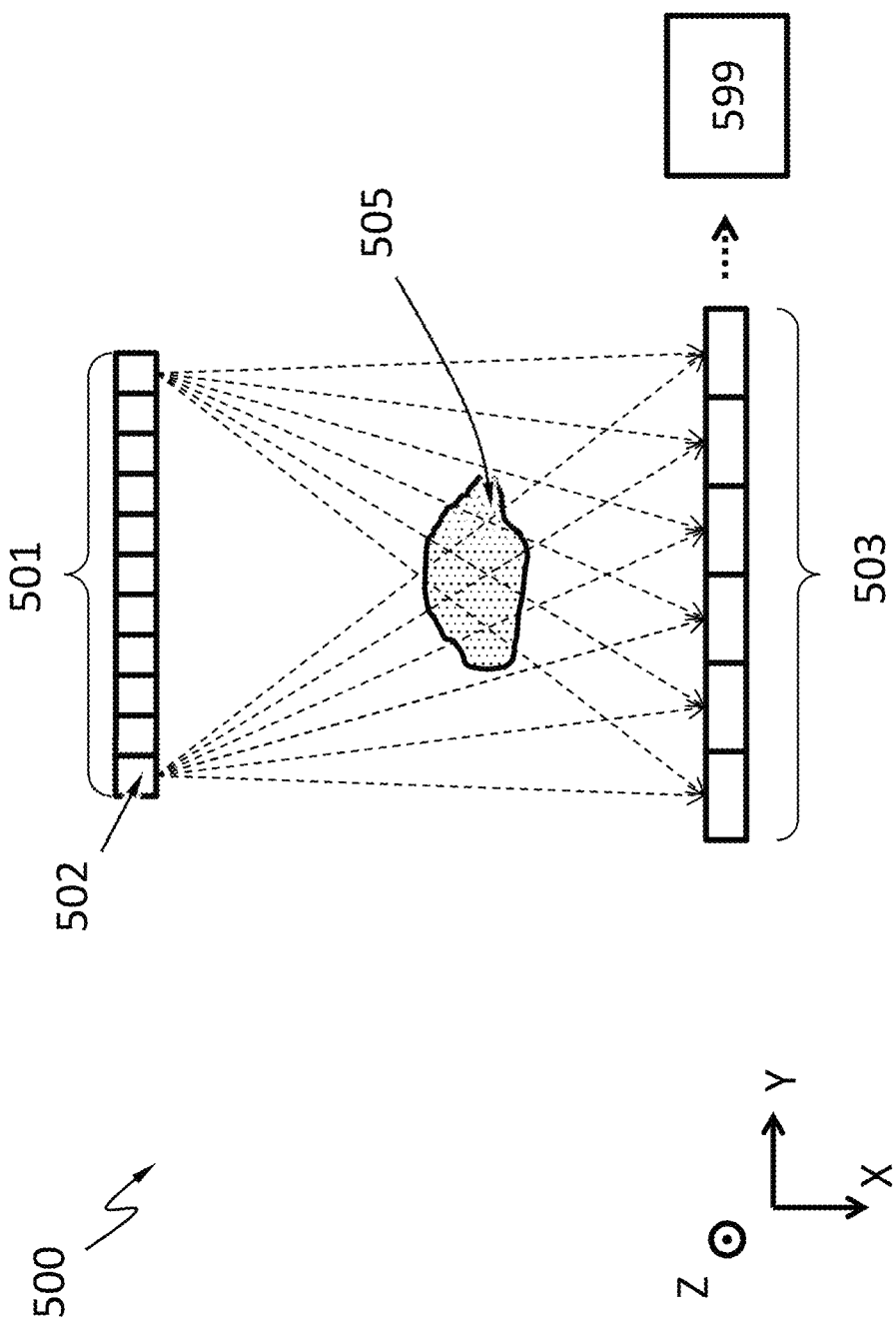
FIG. 3 schematically shows a side view of a source-and-detector assembly, according to an embodiment, which may be suitable to be used in the CT imaging system as shown in FIG. 1.

FIG. 3 schematically shows a side view of a source-and-detector assembly 500, according to an embodiment. The source-and-detector assembly 500 may be suitable to be used in the X-ray CT imaging system 1400. In this example, the source-and-detector assembly 500 includes an X-ray source 501 and an X-ray detector 503. An object 505 may be positioned between the X-ray source 501 and the X-ray detector 503. The object 505 may wholly or partially supported by a sample holder (not shown).

The X-ray source 501 may comprise a plurality of X-ray generators 502. Each X-ray generator 502 may be configured to emit a plurality of X-rays, for example, toward the object 505. The X-rays emitted from different X-ray generators 502 may have different spatial distributions such as different traveling directions. In an embodiment, the plurality of X-ray generators 502 may be arranged in a row. In an embodiment, the plurality of X-ray generators 502 may be arranged in a grid. For example, the plurality of X-ray generators 502 may be arranged in a rectangular array, a hexagonal array, a pentagon array, a honeycomb array, and any other suitable shape of array. The X-ray detector 503 may be configured to detect images of the object 505 formed respectively by the plurality of X-rays from the X-ray source 501. A computer system 599 may be configured to reconstruct a three-dimensional structure of the object 505 based on the images detected by the X-ray detector 503.

Figure 4:
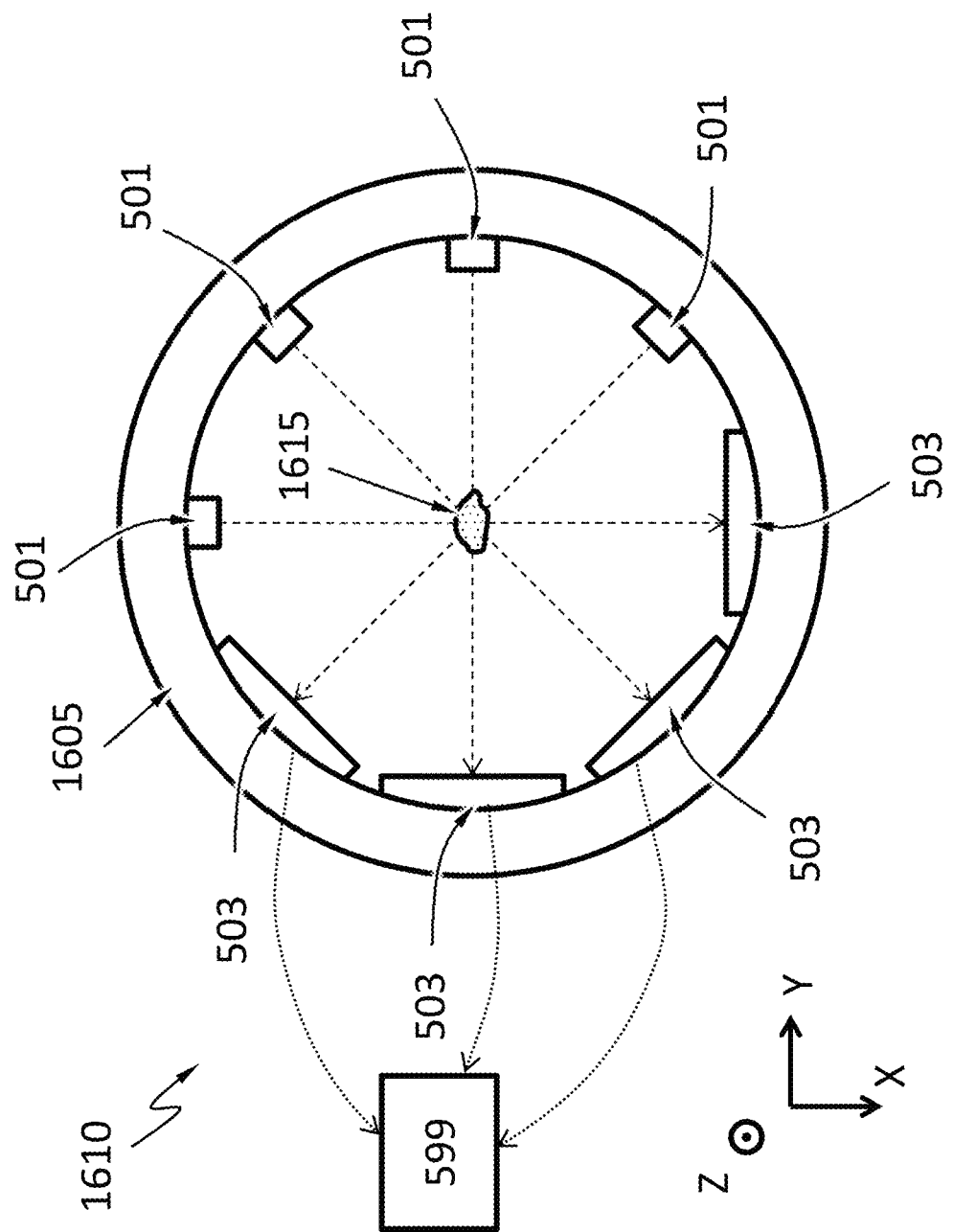
FIG. 4 schematically shows a side view of a source-and-detector assembly, according to an embodiment, which may be suitable to be used in the CT imaging system as shown in FIG. 1.

FIG. 4 schematically shows a side view of a source-and-detector assembly 1610, according to an embodiment. The source-and-detector assembly 1610 may be suitable to be used in the X-ray CT imaging system 1400. In this example, the source-and-detector assembly 1610 includes a plurality of X-ray sources 501, and a plurality of X-ray detectors 503. The plurality of X-ray sources 501 and the plurality of X-ray detectors 503 may be supported by a frame 1605. The plurality of X-ray sources 501 and the plurality of X-ray detectors 503 may be positioned such that each of the X-ray sources 501 is opposite to one of the X-ray detectors 503. One combination of an X-ray source 501 and an X-ray detector 503 opposite thereto and another combination of an X-ray source 501 and an X-ray detector 503 opposite thereto have different orientations.

Each of the X-ray sources 501 may include a plurality of X-ray generators 502. Each X-ray generator 502 may be configured to emit a plurality of X-rays, for example, toward an object 1615. The X-rays emitted from different X-ray generators 502 may have different spatial distributions such as different traveling directions. Each of the X-ray detectors 503 may be configured to detect images of the object 1615 formed respectively by the plurality of X-rays from the X-ray source 501 opposite to that X-ray detector 503. A computer system 599 may be configured to reconstruct a three-dimensional structure of the object 1615 based on the images detected by the X-ray detectors 503.

In an embodiment, the frame 1605 is spherical. Accordingly, as shown, the cross-section of the frame 1605 is circular. In an embodiment, the frame 1605 may be cylindrical. In an embodiment, the object 1615 may be wholly or partially supported on a sample holder (not shown). The plurality of X-ray sources 501 and the plurality of X-ray detectors 503 may be positioned on an inner surface of the frame 1605. The plurality of X-ray sources 501 and the plurality of X-ray detectors 503 may be positioned in the frame 1605 or on an outer surface of the frame 1605 provided that the X-rays from the X-ray sources 501 can pass through the frame 1605. As shown, each of the plurality of X-ray sources 501 may emit X-rays toward the object 1615. The X-ray sources 501 and the X-ray detectors 503 do not have to move or rotate.

In an embodiment, the plurality of X-ray generators 502 in the same X-ray source 501 may emit the plurality of X-rays at different times. The plurality of X-ray generators 502 in different X-ray sources 501 may emit the plurality of X-rays at different times or at the same time.

Figure 5:
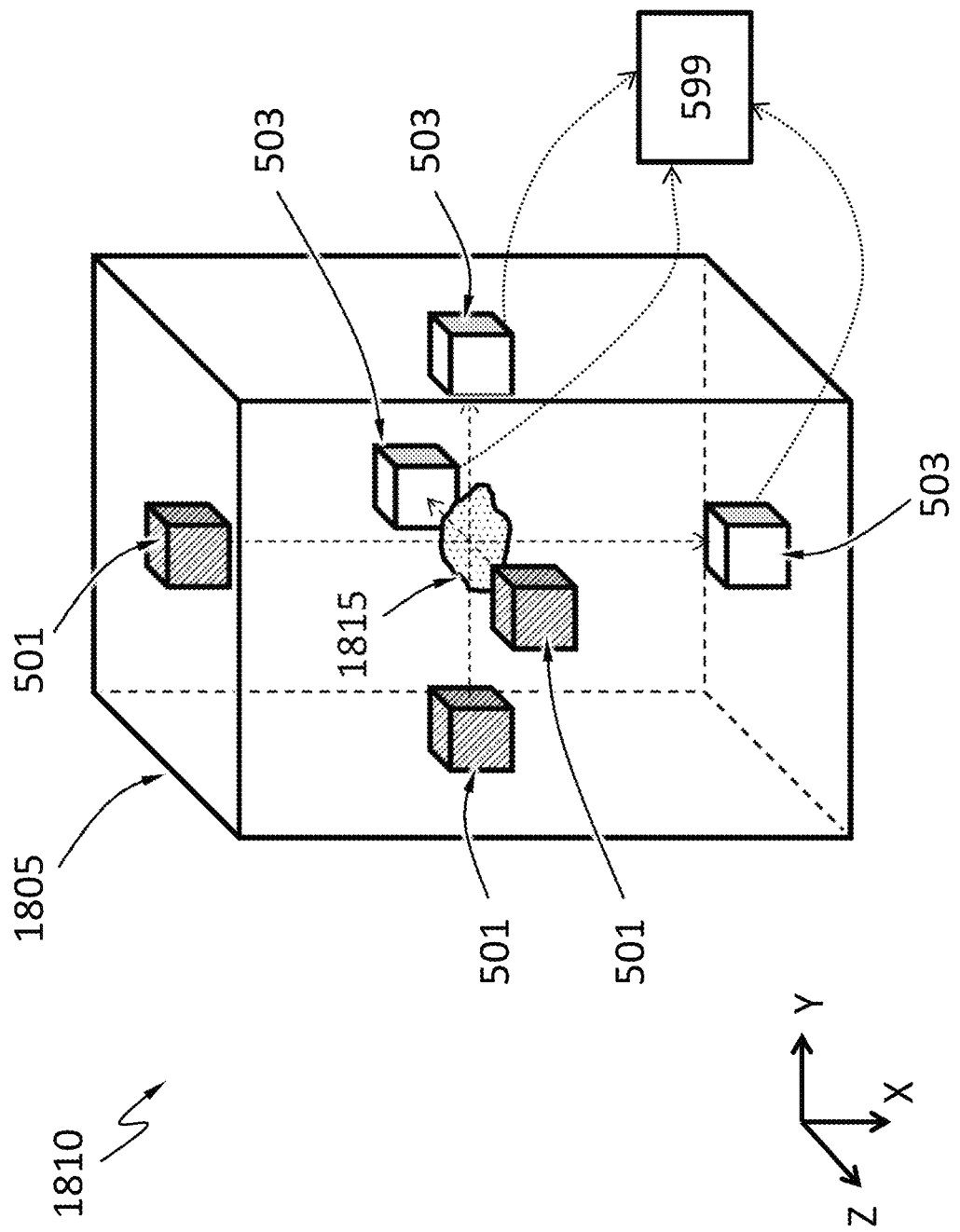
FIG. 5 schematically shows a side view of a source-and-detector assembly, according to an embodiment, which may be suitable to be used in the CT imaging system as shown in FIG. 1.

FIG. 5 schematically shows a view of a source-and-detector assembly 1810, according to an embodiment. The source-and-detector assembly 1810 may be suitable to be used in the X-ray CT imaging system 1400. In this example, the source-and-detector assembly 1810 comprises three X-ray sources 501, and three X-ray detectors 503. The plurality of X-ray sources 501 and the plurality of X-ray detectors 503 may be supported by a frame 1805 that is cubical or cuboidal. The three X-ray sources 501 and the three X-ray detectors 503 may be arranged in three combinations, each of which includes one of the three X-ray sources 501 and one of the three X-ray detectors 503. The X-ray detector 503 and the X-ray source 501 in the same combination are opposite to each other. Different combinations have orientations perpendicular to each other.

Each of the three X-ray sources 501 may include a plurality of X-ray generators 502. Each X-ray generator 502 may be configured to emit a plurality of X-rays, for example, toward an object 1815. The X-rays emitted from different X-ray generators 502 may have different spatial distributions such as different traveling directions. Each of the three X-ray detectors 503 may be configured to detect images of the object 1815 formed respectively by the plurality of X-rays from the X-ray source 501 opposite to that X-ray detector 503. A computer system 599 may be configured to reconstruct a three-dimensional structure of the object 1815 based on the images detected by the X-ray detectors 503.

In an embodiment, the plurality of X-ray generators 502 in the same X-ray source 501 may emit the plurality of X-rays at different times. The plurality of X-ray generators 502 in different X-ray sources 501 may emit the plurality of X-rays at different times or at the same time.

Figure 6:
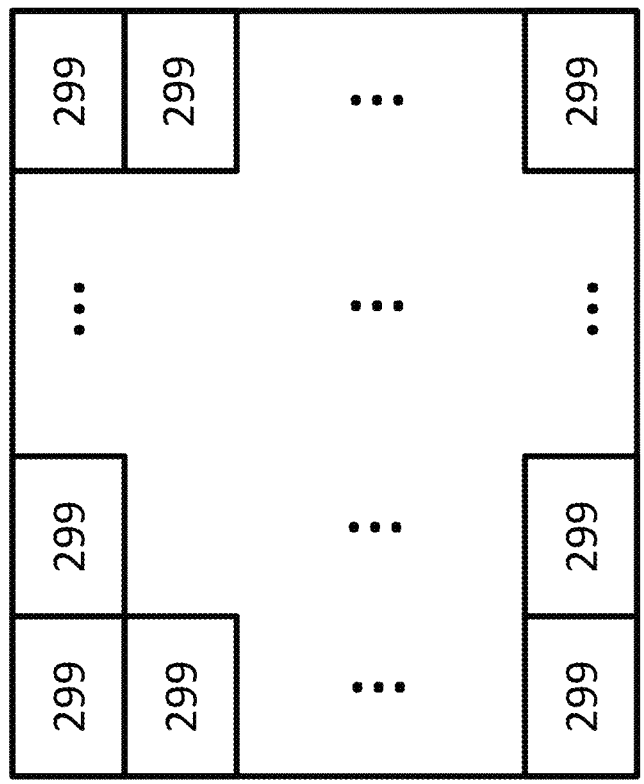
FIG. 6 schematically shows a top view of an X-ray source, according to an embodiment.

FIG. 6 schematically shows a top view of an X-ray source 201, according to an embodiment. In an embodiment, the X-ray source 201 may be the X-ray source 501. As shown, the X-ray source 201 includes a plurality of X-ray generators 299 arranged in an array. The X-ray source 201 may be used as the X-ray source 501 in FIG. 3, FIG. 4 and FIG. 5. In this example, the X-ray source 201 includes a plurality of rows of X-ray generators 299. In some examples, the X-ray source 201 may include only one row or one column of X-ray generators 299. As shown, the plurality of X-ray generators 299 is arranged in a rectangular array. In some other examples, the plurality of X-ray generators 299 may be arranged in a hexagonal array, a pentagon array, a honeycomb array, or any other suitable shape of array.

Figure 7:
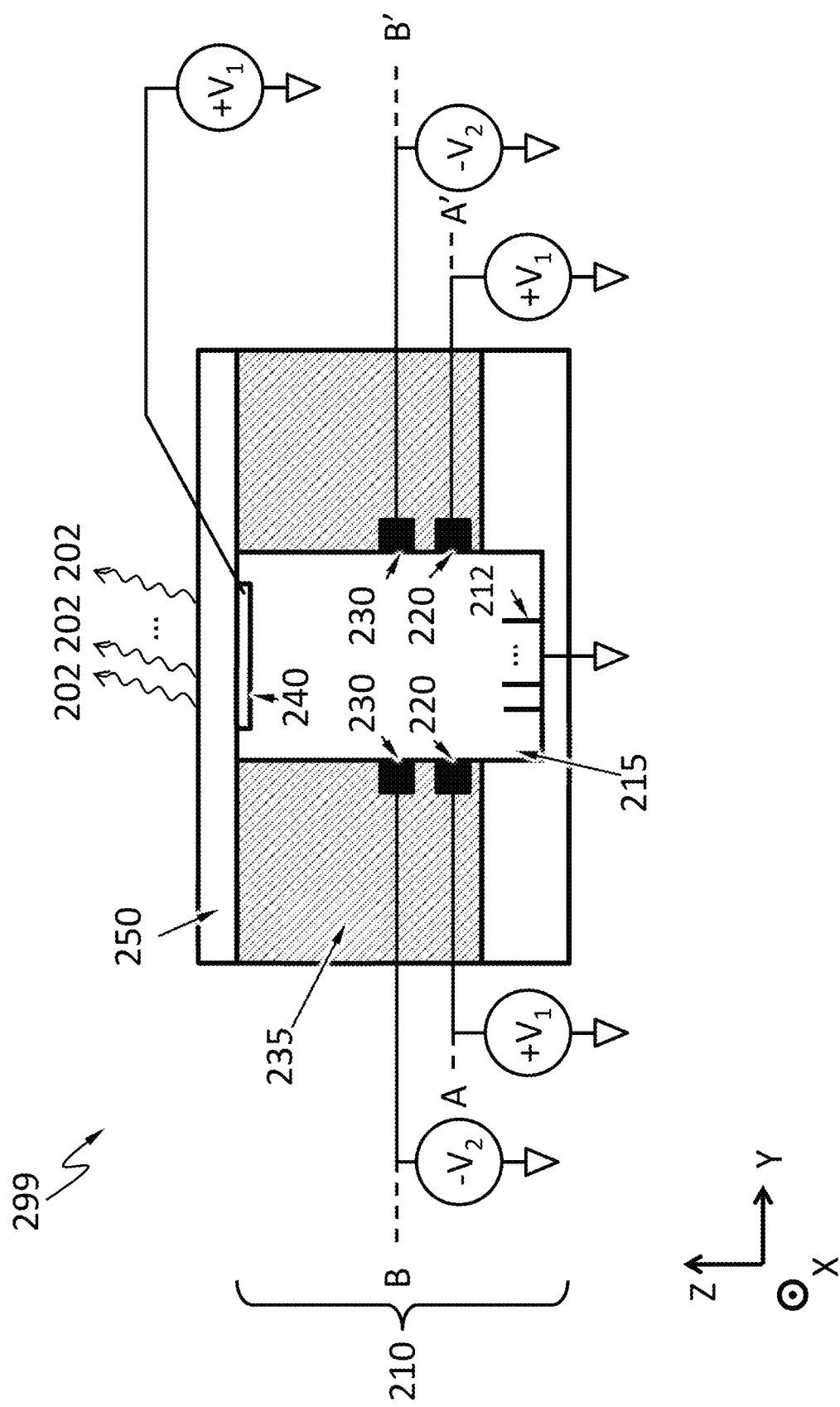
FIG. 7 schematically shows a cross-sectional view of an X-ray generator of the X-ray source, according to an embodiment.

FIG. 7 schematically shows a cross-sectional view of the X-ray generator 299, according to an embodiment. In this example, the X-ray generator 299 includes a first substrate 210, a cathode 212 (e.g., a plurality of carbon nanotubes), a counter electrode 220, optionally a shield electrode 230, a metal anode 240, and optionally a second substrate 250.

In an embodiment, the first substrate 210 may include, but is not limited to, silicon or silicon oxide. As shown, the first substrate 210 has a recess 215. The cathode 212 is formed in the recess 215 of the first substrate 210. The cathode 212 in the recess 215 may include one or more than one carbon nanotubes. The cathode 212 may be configured to emit electrons under an electric field. Electrons may be bound in the cathode 212 (e.g., carbon nanotubes) by a surface potential energy barrier. When a sufficiently strong electrical field is applied (e.g., along the length direction of the carbon nanotubes) to the cathode 212, the electrons in the cathode 212 may acquire sufficient energy and overcome the surface potential energy barrier of the cathode 212 and enter the free space in the recess 215. This mechanism of producing electrons into free space may be referred to as field emission. In an embodiment, the cathode 212 is electrically grounded.

In an embodiment, the counter electrode 220 is on a sidewall of the recess 215. The counter electrode 220 may be biased to a positive voltage of $+V_1$ relative to the cathode 212 thereby provide the electrical field to cause field emission of electrons from the cathode 212. As described above, the electric field established by the positive voltage $+V_1$ may provide the bounded electrons in the cathode 212 with energies greater than the surface potential energy barrier. Also as shown in FIG. 7, the counter electrode 220 may be electrically insulated by an insulator 235 of the first substrate 210.

Figure 8A:
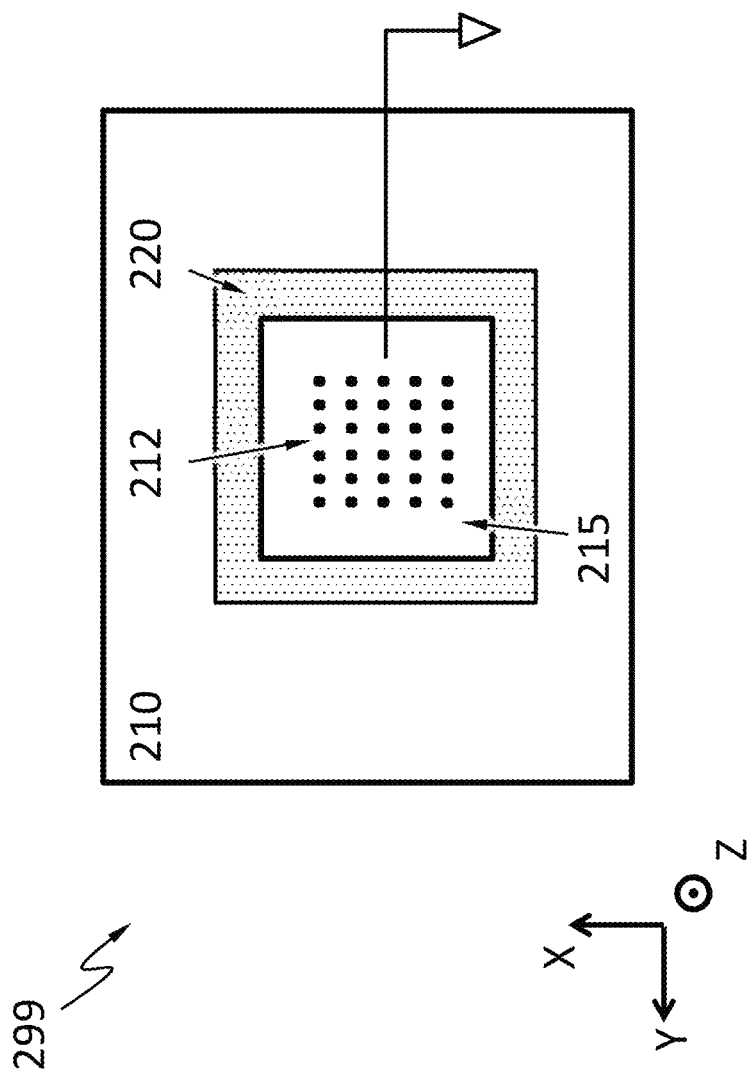
FIG. 8A schematically shows a top view toward a cross-section of the X-ray generator along an A-A' cutline in FIG. 7, according to an embodiment.

FIG. 8A schematically shows a top view toward a cross-section of the X-ray generator 299 along an A-A' cutline in FIG. 7, according to an embodiment. In this example, only the cross sections of the first substrate 210, the cathode 212, the counter electrode 220 and the recess 215 in FIG. 7 are shown. As shown, the cathode 212 may be carbon nanotubes arranged in an array and connected electrically to the ground. In this specific example, the carbon nanotubes are arranged in a rectangular array. However, in some other examples, the nanotubes may be arranged in any other suitable shape of array, including, but not limited to, a circular array, a hexagonal array, a pentagon array, and a honeycomb array. The carbon nanotubes may also have no particular arrangement. Also as shown, the counter electrode 220 may be a continuous ring or dotted ring around the sidewall of the recess 215 of the first substrate 210. Electric connections to the counter electrode 220 are not shown for brevity. In this example, the counter electrode 220 is arranged along the entire perimeter of the sidewall. In some other examples, the counter electrode 220 may be arranged along part of the perimeter of the sidewall. In the example shown in FIG. 8A, the recess 215 has a rectangular cross section and the counter electrode 220 may also be rectangular.

Figure 8B:
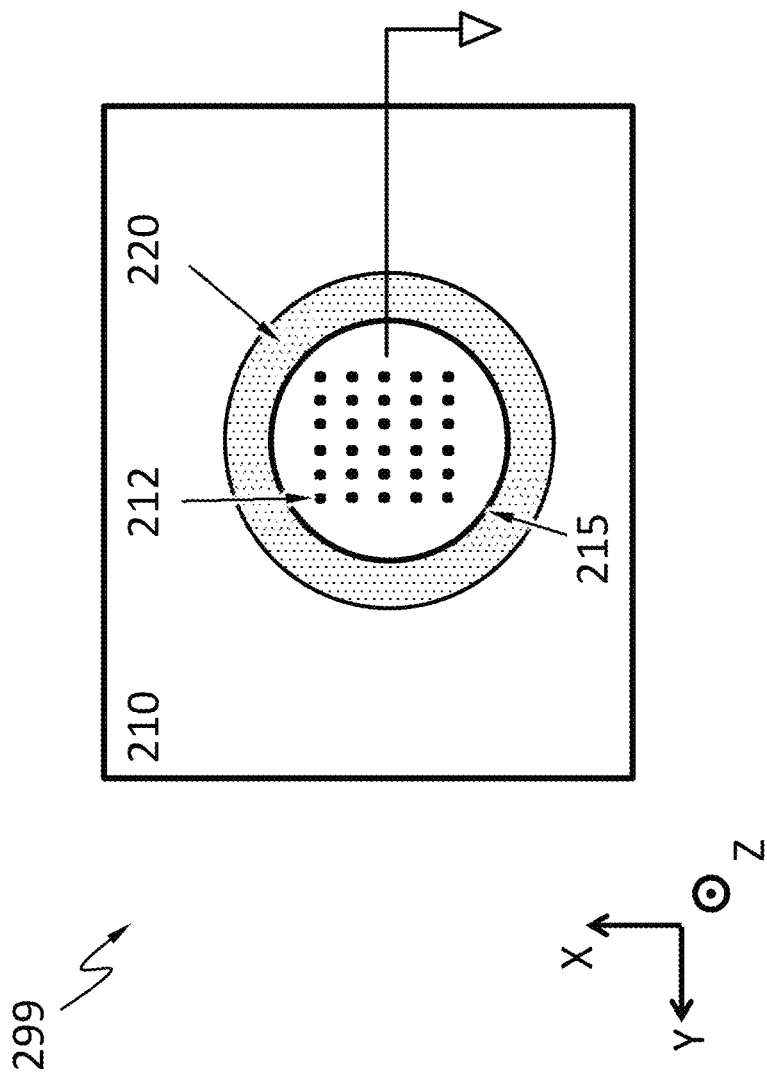
FIG. 8B schematically shows a top view toward a cross-section of the X-ray generator along an A-A' cutline in FIG. 7, according to another embodiment.

FIG. 8B schematically shows the top view toward the cross-section of the X-ray generator 299 along an A-A' cutline in FIG. 7, according to another embodiment. Different from FIG. 8A, the cross section of the recess 215 is circular, and the counter electrode 220 may also be circular.

Returning to FIG. 7, the shield electrode 230 may be on the sidewall of the recess 215 and between the counter electrode 220 and the metal anode 240. The shield electrode 230 may be suitably biased to repel the electrons emitted from the cathode 212 away from the metal anode 240 and thus function as a switch of the X-ray generator 299 (i.e., to enable or disable the generation of the X-ray photons 202 by the X-ray generator 299). As shown, the shield electrode 230 may electrically insulated from the counter electrode 220, and the counter electrode 220 by the insulator 235. Further as shown, the shield electrode 230 may not necessarily be exposed in the recess 215. In an embodiment, the shield electrode 230 may have a similar shape as the counter electrode 220.

When the shield electrode 230 is provided with a sufficiently negative voltage of $-V_2$ relative to the cathode 212, the shield electrode 230 may repel the electrons emitted from the cathode 212 away from the metal anode 240. Without electrons impacting the metal anode 240, the generation of X-ray photons 202 is disabled. When the shield electrode 230 is not sufficiently negatively biased, electrons from the cathode 212 may impact the metal anode 240 and the generation of X-ray photons 202 is enabled.

Figure 9A:
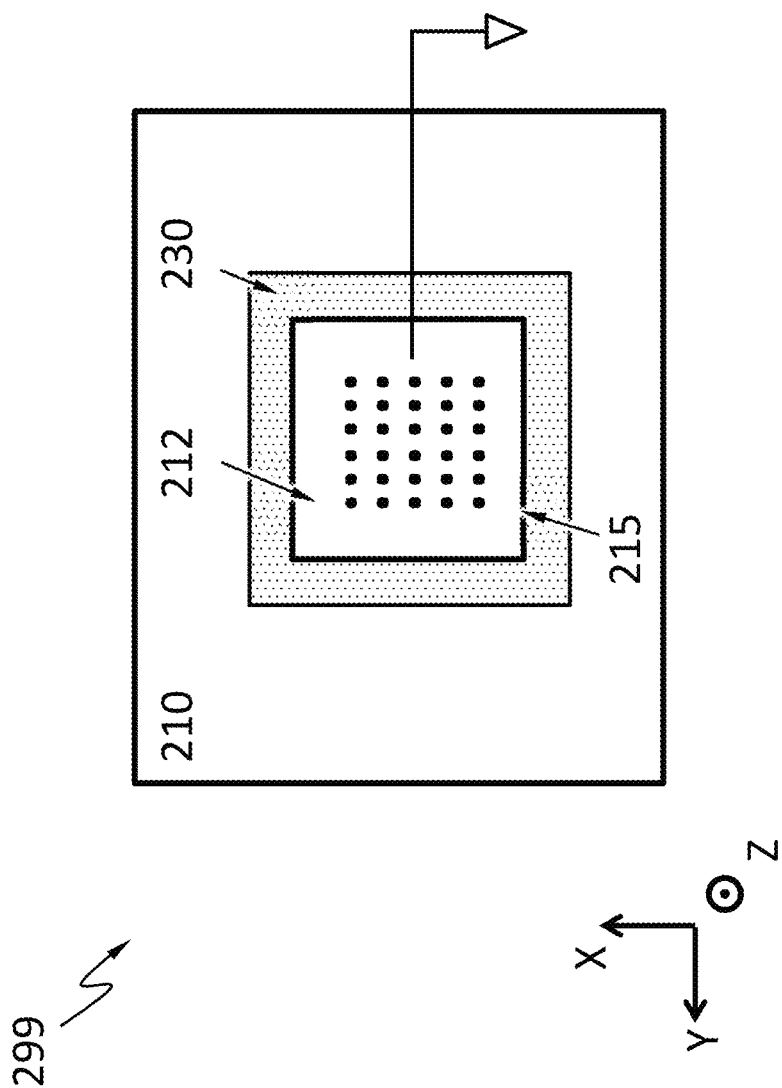
FIG. 9A schematically shows a top view toward a cross-section of the X-ray generator along a B-B' cutline in FIG. 7, according to an embodiment.

FIG. 9A schematically shows a top view toward a cross-section of the X-ray generator 299 along a B-B' cutline in FIG. 7, according to an embodiment. In this example, only the cross sections of the first substrate 210, the cathode 212, and the shield electrode 230 in FIG. 7 are shown. As shown, the cathode 212 may be carbon nanotubes arranged in an array and connected electrically to the ground. In this specific example, the carbon nanotubes are arranged in a rectangular array. However, in some other examples, the nanotubes may be arranged in any other suitable shape of array, including, but not limited to, a circular array, a hexagonal array, a pentagon array, and a honeycomb array. The carbon nanotubes may also have no particular arrangement. Also as shown, the shield electrode 230 may be a continuous ring or dotted ring around the sidewall of the recess 215 of the first substrate 210. Electric connections to the shield electrode 230 are not shown for brevity. In this example, the shield electrode 230 is arranged along the entire perimeter of the sidewall. In some other examples, the shield electrode 230 may be arranged along part of the perimeter of the sidewall. In the example shown in FIG. 9A, the recess 215 has a rectangular cross section and the shield electrode 230 may also be rectangular.

Figure 9B:
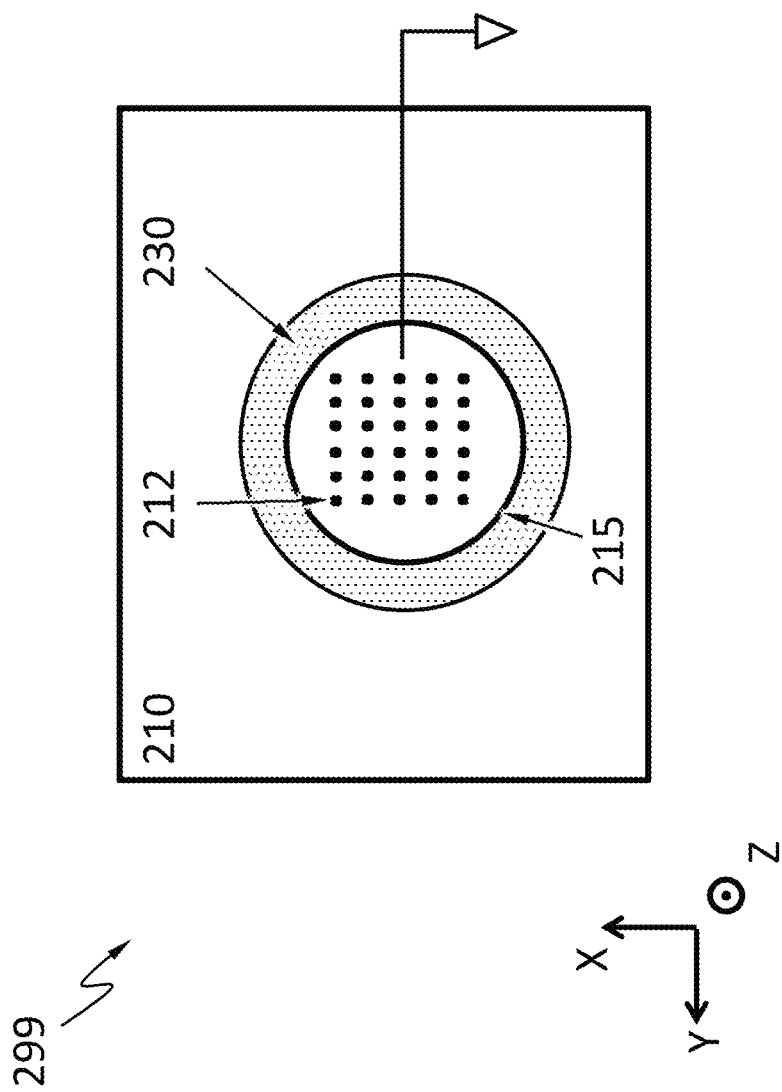
FIG. 9B schematically shows a top view toward a cross-section of the X-ray generator along a B-B' cutline in FIG. 7, according to another embodiment.

FIG. 9B schematically shows the top view toward the cross-section of the X-ray generator 299 along a B-B' cutline in FIG. 7, according to another embodiment. Different from FIG. 9A, the cross section of the recess 215 is circular, and the shield electrode 230 may also be circular.

Returning to FIG. 7, in an embodiment, the second substrate 250 may be a glass substrate or a substrate that has low attenuation of X-ray of interest. In an embodiment, the second substrate 250 may include, but is not limited to, silicon or silicon oxide. The second substrate 250 may allow X-ray photons 202 to pass through. As shown, the metal anode 240 is beneath the second substrate 250 (i.e., on the side facing the cathode 212), which are collectively situated on the insulator 235. In another embodiment, the metal anode 240 may be dispose over the recess 215 without the second substrate 250.

The metal anode 240 may be biased to a positive voltage of $+V_3$ relative to the cathode 212. The electrons from the cathode 212, if not repelled by the shield electrode 230, are accelerated by an electric field established by this voltage toward the metal anode 240. The metal anode 240 may include, but is not limited to, tungsten, molybdenum, rhenium, copper, or their combinations. When the electrons gain enough kinetic energy (e.g., greater than 10 KeV, 50 KeV, 80 KeV, 100K eV, 130 KeV, etc.) before hitting the metal anode 240, the X-ray photons 202 may be generated after the high speed free electrons impact the metal anode 240. As shown in FIG. 7, the generated X-ray photons 202 travel in parallel. In some other examples, the generated X-ray photons 202 may travel in different directions.

Figure 10:
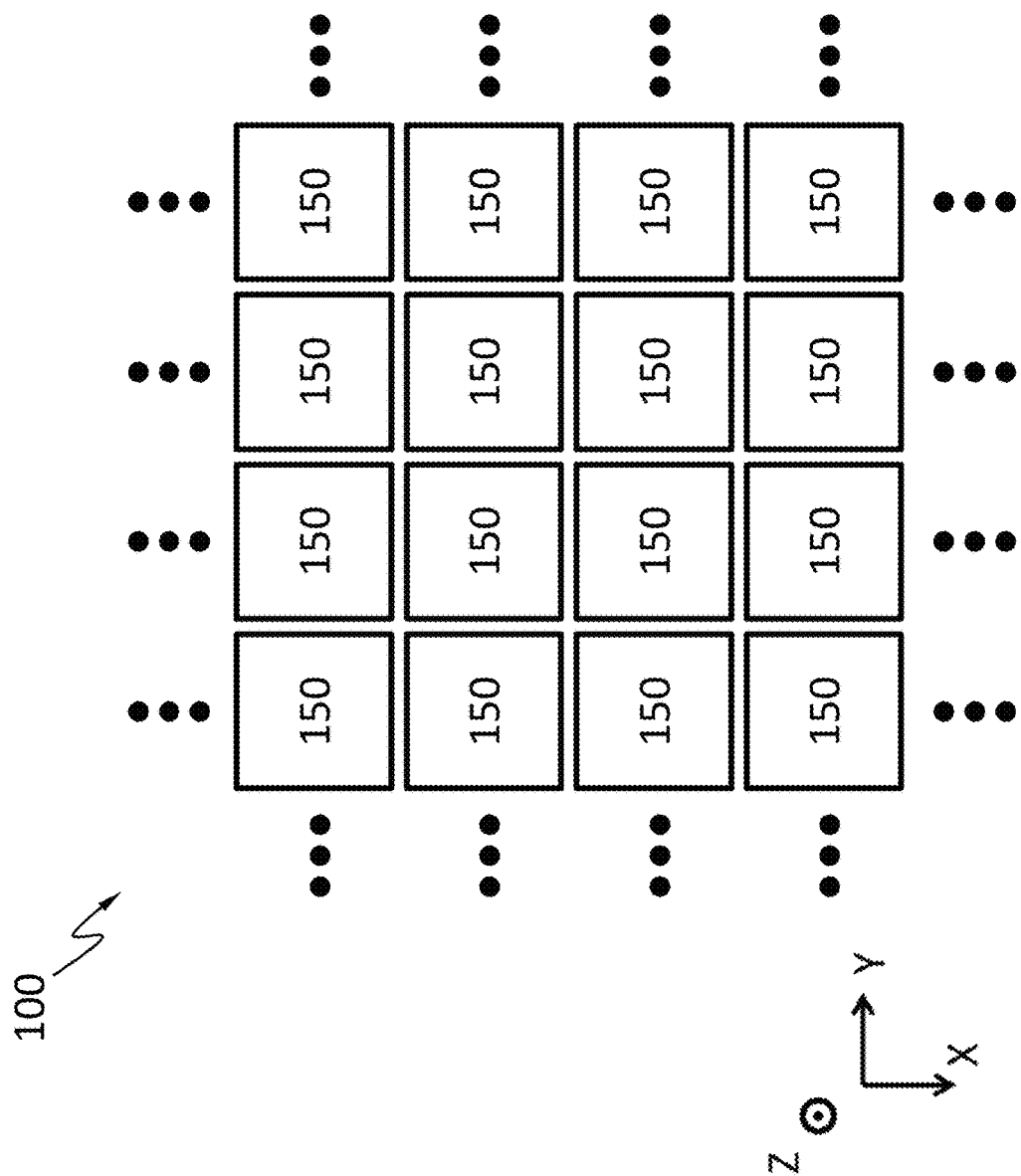
FIG. 10 schematically shows an X-ray detector, according to an embodiment.

FIG. 10 schematically shows an X-ray detector 100, according to an embodiment. In an embodiment, the X-ray detector 100 may be used as the X-ray detector 503 in FIG. 3, FIG. 4 and FIG. 5. The X-ray detector 100 may be planar. The detector has an array of pixels 150. The array may be a rectangular array, a pentagon array, a honeycomb array, a hexagonal array or any other suitable array. Each pixel 150 is configured to detect an X-ray photon incident thereon and measure the energy of the X-ray photon. For example, each pixel 150 is configured to count numbers of X-ray photons incident thereon whose energy falls in a plurality of bins, within a period of time. All the pixels 150 may be configured to count the numbers of X-ray photons incident thereon within a plurality of bins of energy within the same period of time. Each pixel 150 may have its own analog-to-digital converter (ADC) configured to digitize an analog signal representing the energy of an incident X-ray photon into a digital signal. For XRF applications, an ADC with a 10-bit resolution or higher is useful. Each pixel 150 may be configured to measure its dark current, such as before or concurrently with each X-ray photon incident thereon. Each pixel 150 may be configured to deduct the contribution of the dark current from the energy of the X-ray photon incident thereon. The pixels 150 may be configured to operate in parallel. For example, when one pixel 150 measures an incident X-ray photon, another pixel 150 may be waiting for an X-ray photon to arrive. The pixels 150 may not have to be individually addressable.

The detector 100 may have at least 100, 2500, 10000, or more pixels 150. The detector 100 may be configured to add the numbers of X-ray photons for the bins of the same energy range counted by all the pixels 150. For example, the detector 100 may add the numbers the pixels 150 stored in a bin for energy from 70 KeV to 71 KeV, add the numbers the pixels 150 stored in a bin for energy from 71 KeV to 72 KeV, and so on. The detector 100 may compile the added numbers for the bins as a spectrum of the X-ray photons incident on the detector 100.

Figure 11A:
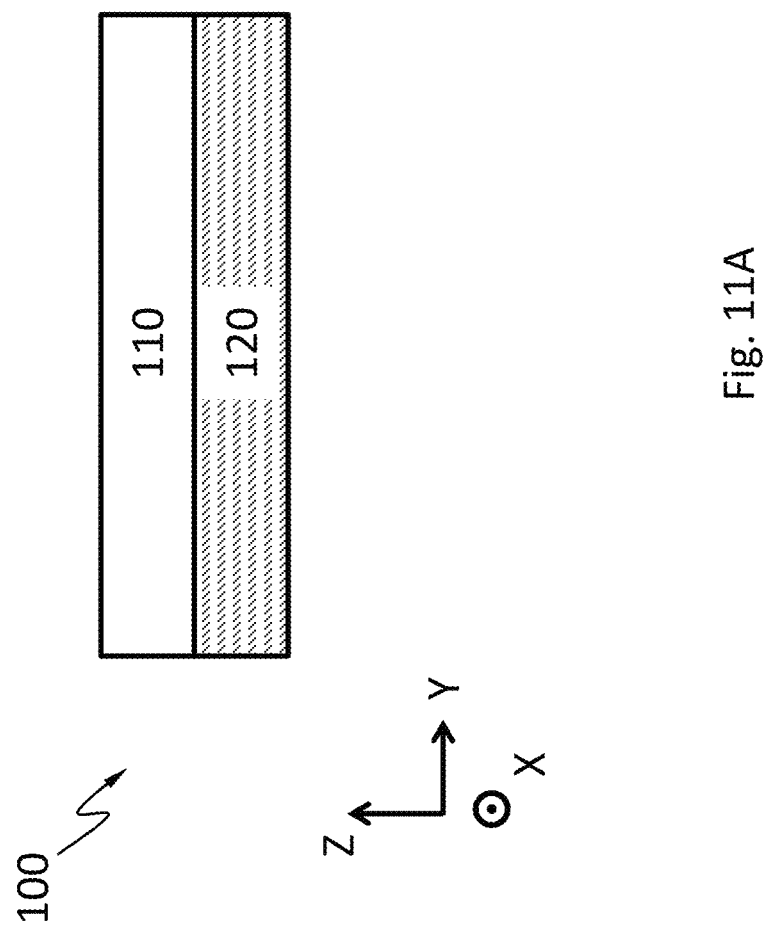
FIG. 11A schematically shows a cross-sectional view of the detector, according to an embodiment.

FIG. 11A schematically shows a cross-sectional view of the detector 100, according to an embodiment. The detector 100 may include an X-ray absorption layer 110 and an electronics layer 120 (e.g., an ASIC) for processing or analyzing electrical signals incident X-ray generates in the X-ray absorption layer 110. In an embodiment, the detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 11B:
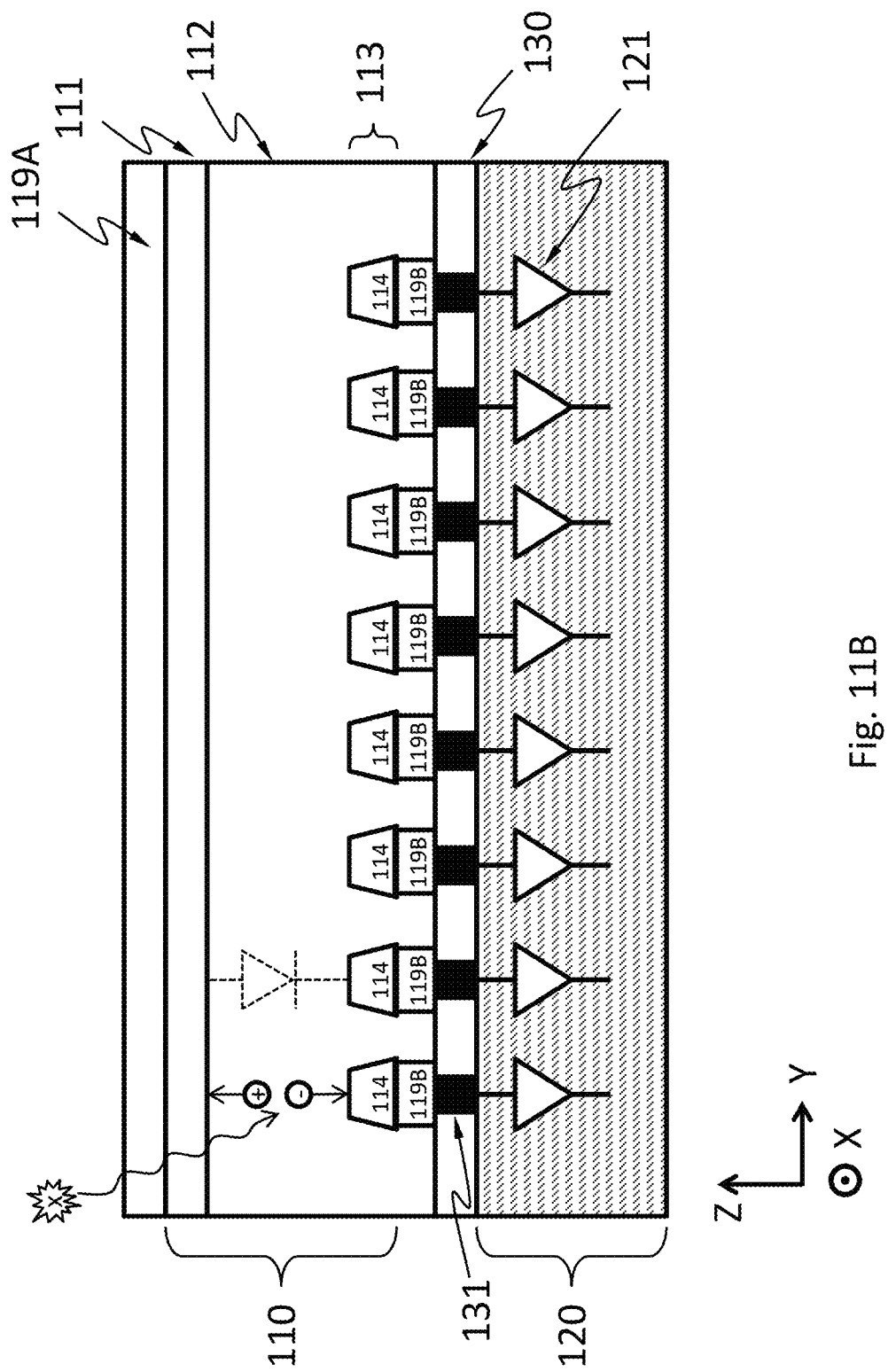
FIG. 11B schematically shows a detailed cross-sectional view of the detector, according to an embodiment.

As shown in a detailed cross-sectional view of the detector 100 in FIG. 11B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 11B, each of the discrete regions 114 of the second doped region 113 forms a diode with the first doped region 111 and the optional intrinsic region 112. Namely, in the example in FIG. 11B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single X-ray photon are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by an X-ray photon incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by an X-ray photon incident therein flow to the discrete region 114. Namely, less than 2%, less than 1%, less than 0.1%, or less than 0.01% of these charge carriers flow beyond the pixel.

Figure 11C:
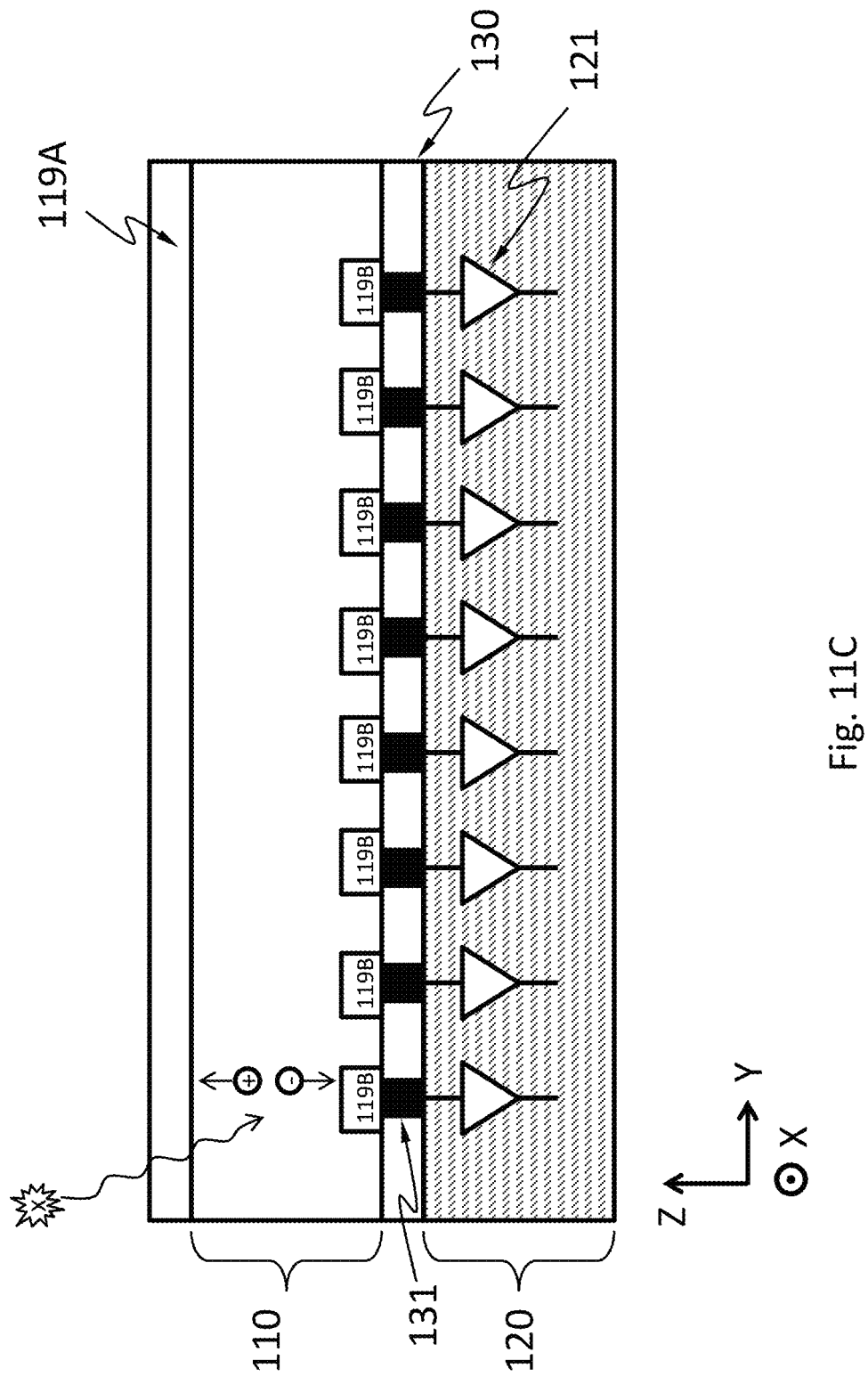
FIG. 11C schematically shows an alternative detailed cross-sectional view of the detector, according to an embodiment.

As shown in an alternative detailed cross-sectional view of the detector 100 in FIG. 11C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single X-ray photon are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by an X-ray photon incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by an X-ray photon incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 12A:
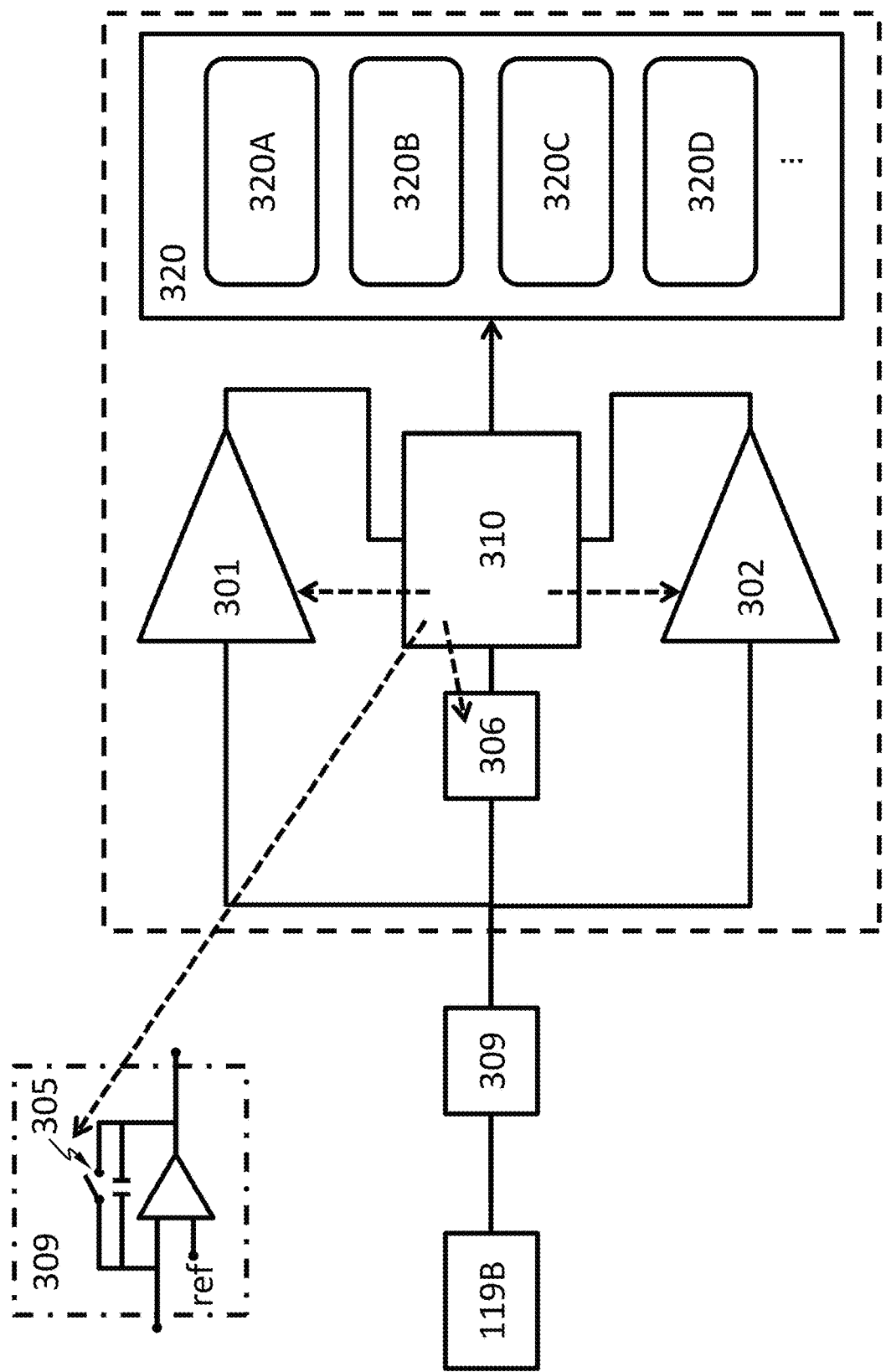
FIG. 12A and FIG. 12B each schematically show a component diagram of the electronic system of the detector, according to an embodiment.
Figure 12B:
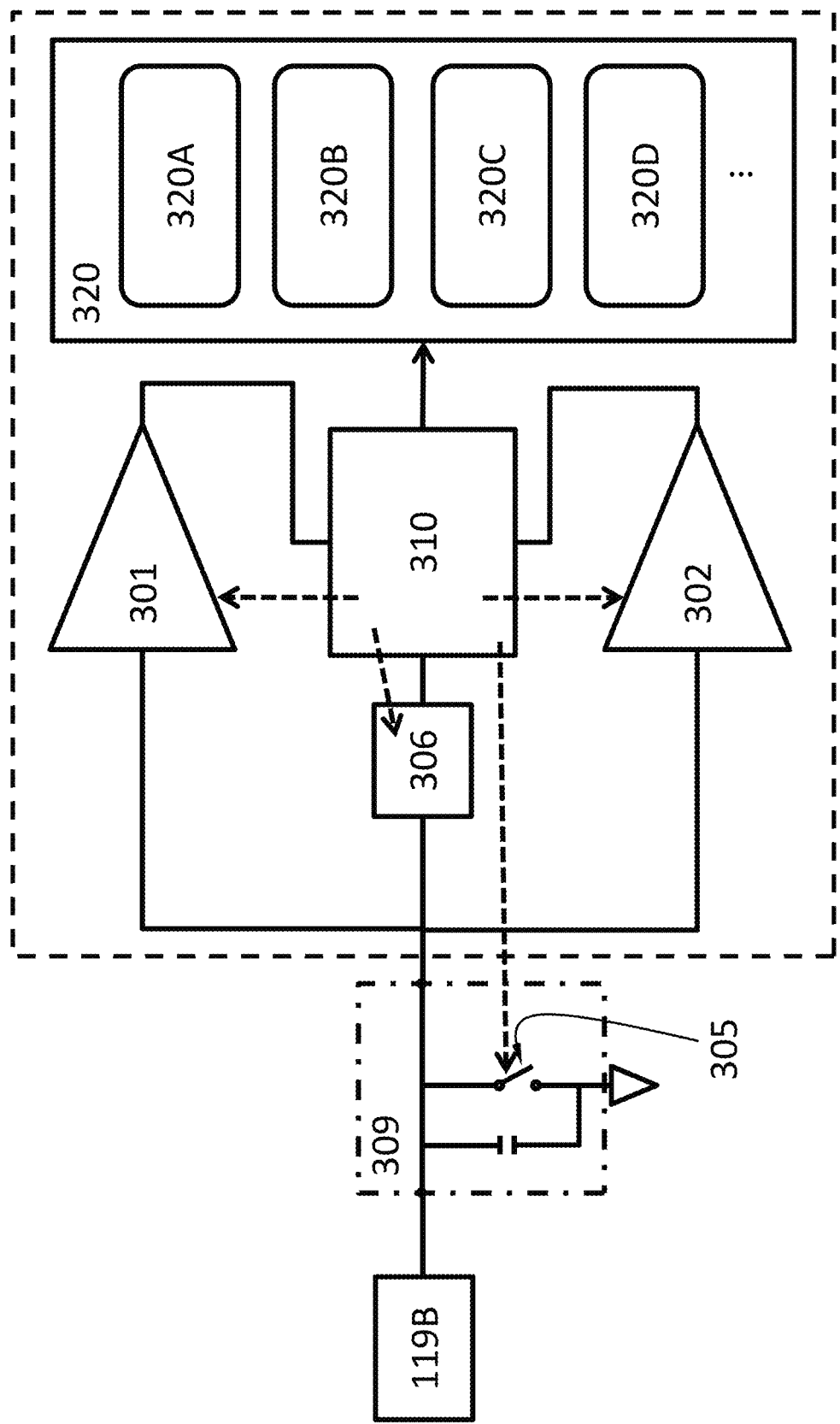

FIG. 12A and FIG. 12B each show a component diagram of the electronic system 121, according to an embodiment. The electronic system 121 may include a first voltage comparator 301, a second voltage comparator 302, a plurality of counters 320 (including counters 320A, 320B, 320C, 320D . . . ), a switch 305, an ADC 306 and a controller 310.

The first voltage comparator 301 is configured to compare the voltage of a discrete portion of the electric contact 119B to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 1-5%, 5-10%, 10%-20%, 20-30%, 30-40% or 40-50% of the maximum voltage one incident X-ray photon may generate on the electric contact 119B. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counters 320 may be a software component (e.g., numbers stored in a computer memory) or a hardware component (e.g., 4017 IC and 7490 IC). Each counter 320 is associated with a bin for an energy range. For example, counter 320A may be associated with a bin for 70-71 KeV, counter 320B may be associated with a bin for 71-72 KeV, counter 320C may be associated with a bin for 72-73 KeV, counter 320D may be associated with a bin for 73-74 KeV. When the energy of an incident X-ray photons is determined by the ADC 306 to be in the bin a counter 320 is associated with, the number registered in the counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire after the voltage becomes stable, i.e., the rate of change of the voltage is substantially zero. The phase "the rate of change is substantially zero" means that temporal change is less than 0.1%/ns. The phase "the rate of change is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by one of the counters 320 to increase by one, if, during the time delay, the second voltage comparator 302 determines that the absolute value of the voltage equals or exceeds the absolute value of the second threshold, and the energy of the X-ray photon falls in the bin associated with the counter 320.

The controller 310 may be configured to cause the ADC 306 to digitize the voltage upon expiration of the time delay and determine based on the voltage which bin the energy of the X-ray photon falls in.

The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The ADC 306 may feed the voltage it measures to the controller 310 as an analog or digital signal. The ADC may be a successive-approximation-register (SAR) ADC (also called successive approximation ADC). An SAR ADC digitizes an analog signal via a binary search through all possible quantization levels before finally converging upon a digital output for the analog signal. An SAR ADC may have four main subcircuits: a sample and hold circuit to acquire the input voltage ($V_{in}$), an internal digital-analog converter (DAC) configured to supply an analog voltage comparator with an analog voltage equal to the digital code output of the successive approximation register (SAR), the analog voltage comparator that compares $V_{in}$ to the output of the internal DAC and outputs the result of the comparison to the SAR, the SAR configured to supply an approximate digital code of $V_{in}$ to the internal DAC. The SAR may be initialized so that the most significant bit (MSB) is equal to a digital 1. This code is fed into the internal DAC, which then supplies the analog equivalent of this digital code ($V_{ref}/2$) into the comparator for comparison with $V_{in}$. If this analog voltage exceeds $V_{in}$, the comparator causes the SAR to reset this bit; otherwise, the bit is left a 1. Then the next bit of the SAR is set to 1 and the same test is done, continuing this binary search until every bit in the SAR has been tested. The resulting code is the digital approximation of $V_{in}$ and is finally output by the SAR at the end of the digitization.

Figure 13:
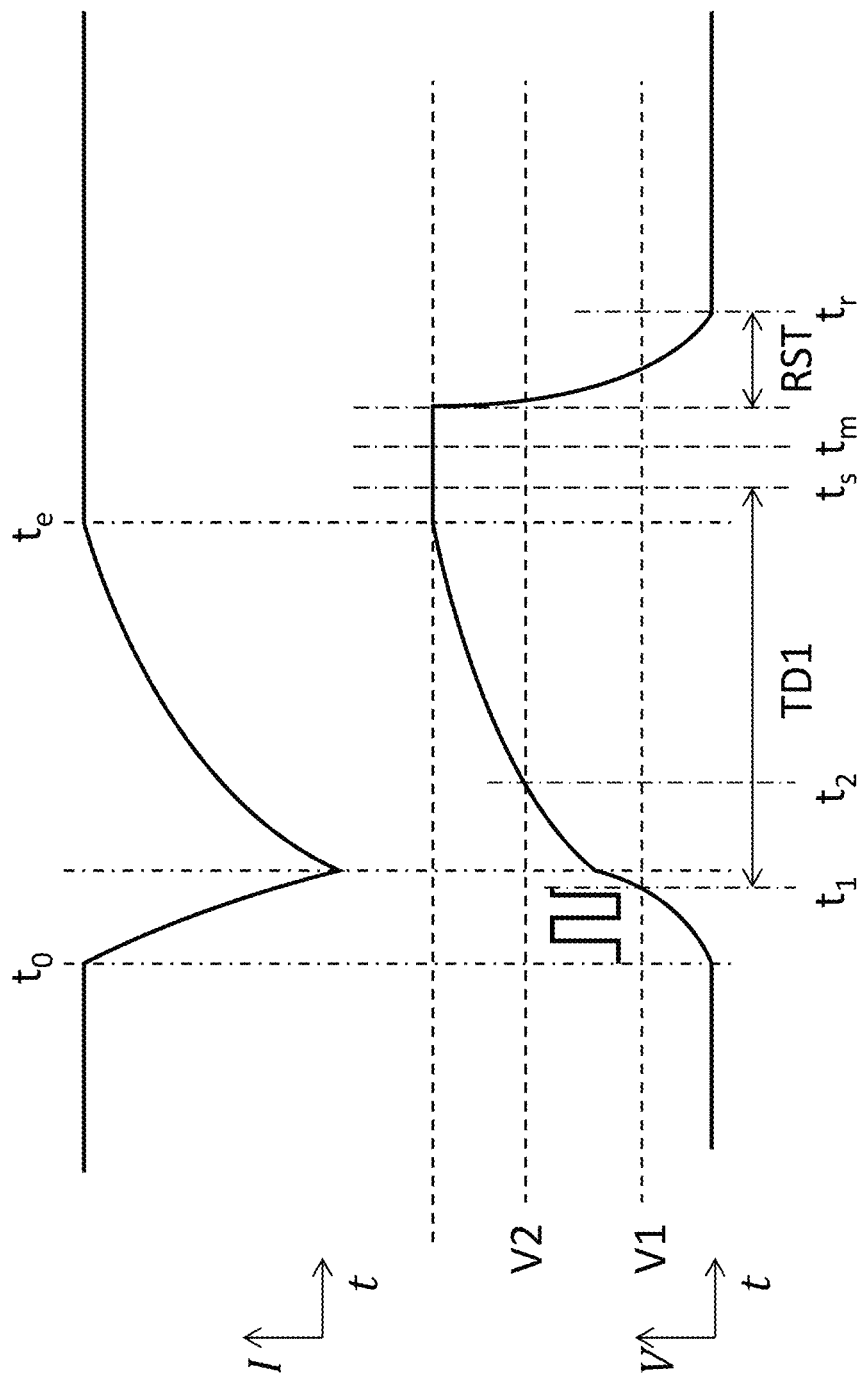
FIG. 13 schematically shows a temporal change of the electric current flowing through an electric contact (upper curve) caused by charge carriers generated by an X-ray photon incident on a pixel associated with the electric contact, and a corresponding temporal change of the voltage of the electric contact (lower curve).

The system 121 may include a capacitor module 309 electrically connected to the electric contact 119B, wherein the capacitor module is configured to collect charge carriers from the electric contact 119B. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 13, between $t_s$ to $t_0$). After the integration period has expired, the capacitor voltage is sampled by the ADC 306 and then reset by a reset switch. The capacitor module 309 can include a capacitor directly connected to the electric contact 119B.

FIG. 13 schematically shows a temporal change of the electric current flowing through the electric contact 119B (upper curve) caused by charge carriers generated by an X-ray photon incident on the pixel 150 associated with the electric contact 119B, and a corresponding temporal change of the voltage of the electric contact 119B (lower curve). The voltage may be an integral of the electric current with respect to time. At time $t_0$, the X-ray photon hits the diode or the resistor, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 waits for stabilization of the voltage to stabilize. The voltage stabilizes at time $t_e$, when all charge carriers generated by the X-ray photon drift out of the X-ray absorption layer 110. At time $t_s$, the time delay TD1 expires. At or after time $t_e$, the controller 310 causes the ADC 306 to digitize the voltage and determines which bin the energy of the X-ray photons falls in. The controller 310 then causes the number registered by the counter 320 corresponding to the bin to increase by one. In the example of FIG. 11, time $t_s$ is after time $t_e$; namely TD1 expires after all charge carriers generated by the X-ray photon drift out of the X-ray absorption layer 110. If time $t_e$ cannot be easily measured, TD1 can be empirically chosen to allow sufficient time to collect essentially all charge carriers generated by an X-ray photon but not too long to risk have another incident X-ray photon. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the X-ray photon, which relates to the energy of the X-ray photon. The controller 310 may be configured to determine the bin the energy of the X-ray photon falls in, based on the output of the ADC 306.

After TD1 expires or digitization by the ADC 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident X-ray photon. Implicitly, the rate of incident X-ray photons the system 121 can handle in the example of FIG. 11 is limited by 1/(TD1+RST). If the first voltage comparator 301 has been deactivated, the controller 310 can activate it at any time before RST expires. If the controller 310 has been deactivated, it may be activated before RST expires.

Because the detector 100 has many pixels 150 that may operate in parallel, the detector can handle much higher rate of incident X-ray photons. This is because the rate of incidence on a particular pixel 150 is 1/N of the rate of incidence on the entire array of pixels, where N is the number of pixels.

Figure 14:
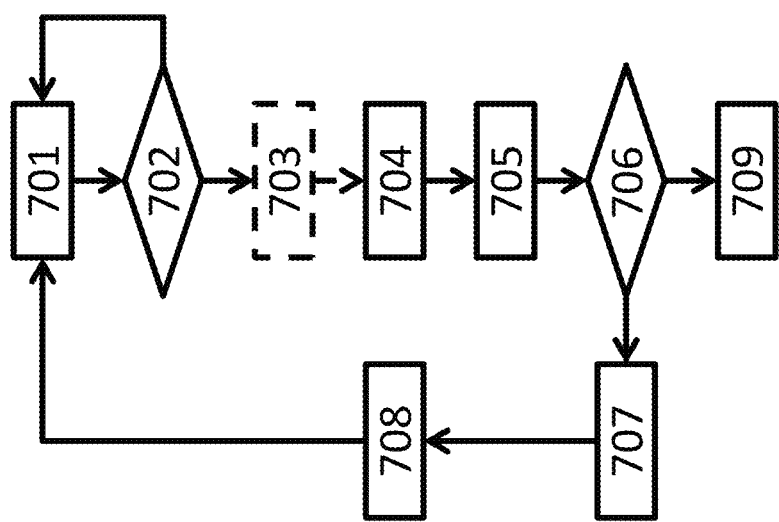
FIG. 14 shows an example flow chart for measuring energy of an X-ray photon by an X-ray detector, according to an embodiment.
Figure 15:
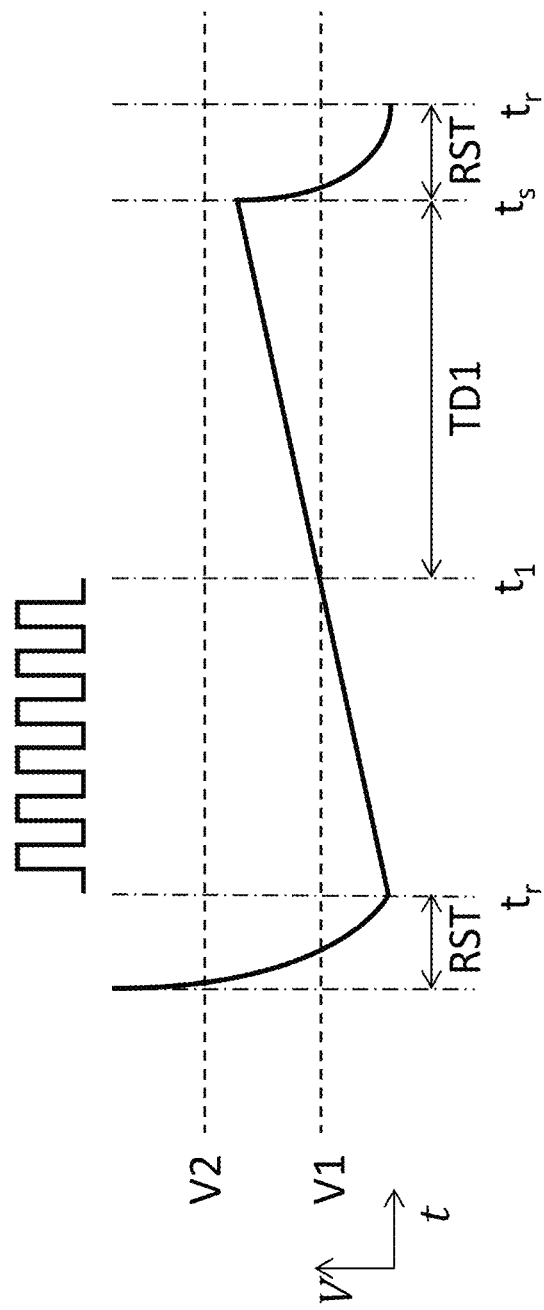
FIG. 15 schematically shows a temporal change of the voltage of the electric contact caused by the dark current, according to an embodiment.

FIG. 14 shows an example flow chart for measuring energy of an X-ray photon by an X-ray detector (e.g., the X-ray detectors 100), according to an embodiment. In step 701, compare, e.g., using the first voltage comparator 301, a voltage of an electric contact 119B of a diode or a resistor exposed to X-ray photons (e.g., fluorescent X-ray), to the first threshold. In step 702, determine, e.g., with the controller 310, whether the absolute value of the voltage equals or exceeds the absolute value of the first threshold V1. If the absolute value of the voltage does not equal or exceed the absolute value of the first threshold, the method goes back to step 701. If the absolute value of the voltage equals or exceeds the absolute value of the first threshold, continue to step 703. In step 703, measure $T=(t_1-t_0)$. In step 704, start, e.g., using the controller 310, the time delay TD1. In step 705, compare, e.g., using the second voltage comparator 302, the voltage to the second threshold. In step 706, determine, e.g., using the controller 310, whether the absolute value of the voltage equals or exceeds the absolute value of the second threshold V2. If the absolute value of the voltage does not equal or exceed the absolute value of the second threshold, the method goes to step 707. In step 707, measure the contribution of the dark current to the voltage using T. In an example, determine whether T is greater than the largest T previously measured ($T_{max}$). $T_{max}=0$ if T is not previously measured. If T is greater than $T_{max}$, replace $T_{max}$ with T (i.e., T becomes the new $T_{max}$). The contribution of the dark current to the voltage is at a rate of $V1/T_{max}$. If the dark current is measured as in this example, the contribution of the dark current in step 709 is $((t_m-t_r) \cdot V1/T_{max})$, where $t_r$ is the end of the last reset period. $(t_m-t_r)$, like any time intervals in this disclosure, can be measured by counting pulses (e.g., counting clock cycles or clock pulses). $T_{max}$ may be reset to zero before each measurement with the detector 100. T may be measured by counting the number of pulses between $t_1$ and $t_0$, as schematically shown in FIG. 13 and FIG. 15. Another way to measure the contribution of the dark current to the voltage using T includes extracting a parameter of the distribution of T (e.g., the expected value of T ($T_{expected}$)) and estimate the rate of the contribution of the dark current to the voltage as $V1/T_{expected}$. In step 708, reset the voltage to an electrical ground, e.g., by connecting the electric contact 119B to an electrical ground. If the absolute value of the voltage equals or exceeds the absolute value of the second threshold, continue to step 709. In step 709, measure the voltage after it stabilizes, at time $t_m$, and subtract a contribution from a dark current to the measured voltage. Time $t_m$ can be any time after TD1 expires and before RST. The time when the reset period ends (e.g., the time when the electric contact 119B is disconnected from the electrical ground) is $t_r$.

FIG. 15 schematically shows a temporal change of the voltage of the electric contact 119B caused by the dark current, according to an embodiment. After RST, the voltage increase due to the dark current. The higher the dark current, the less time it takes for the voltage to reach V1 (namely shorter T). Therefore, T is a measure of the dark current. The dark current is unlikely large enough to cause the voltage to reach V2 during TD1 but current caused by an incident X-ray photon is probably large enough to do so. This difference may be used to identify the effect of the dark current. The flow in FIG. 15 may be carried out in each pixel 150 as the pixel 150 measures a series of incident X-ray photons, which will allow capturing the changes of the dark current (e.g., caused by changing environment such as temperature).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   a first X-ray source comprising a plurality of X-ray generators configured to respectively emit a plurality of X-rays toward an object; and
   a first X-ray detector configured to detect images of the object formed respectively by the plurality of X-rays from the first X-ray source;
   wherein each of the plurality of X-ray generators comprises:
      a cathode in a recess of a first substrate;
      a counter electrode on a sidewall of the recess, configured to cause field emission of electrons from the cathode; and
      a metal anode configured to receive the electrons emitted from the cathode and to emit X-ray from impact by the electrons on the metal anode.

2. The system of claim 1, further comprising a computer system configured to reconstruct a three-dimensional structure of the object based on the images.

3. The system of claim 1, wherein the plurality of X-ray generators are configured to emit X-rays at different times.

4. The system of claim 1, wherein the plurality of X-ray generators are arranged in a row or in a grid.

5. The system of claim 4, wherein the grid is selected from a group consisting of a rectangular array, a hexagonal array, a pentagon array, and a honeycomb array.

6. The system of claim 1, wherein the plurality of X-rays have different spatial distributions.

7. The system of claim 1, wherein the cathode comprises a plurality of carbon nanotubes.

8. The system of claim 1, wherein the counter electrode is a continuous ring or dotted ring around the sidewall.

9. The system of claim 1, further comprising a shield electrode between the counter electrode and the metal anode, the shield electrode configured to repel the electrons facing the metal anode.

10. The system of claim 9, wherein the shield electrode is a continuous ring or dotted ring around the sidewall.

11. The system of claim 1, wherein the first substrate comprises silicon or silicon oxide.

12. The system of claim 1, wherein the metal anode comprises one or more metals selected from a group consisting of tungsten, molybdenum, rhenium, copper and combinations thereof.

13. The system of claim 1, further comprising a second substrate bonded to the first substrate, wherein the second substrate covers the recess.

14. The system of claim 13, wherein the metal anode is supported by the second substrate.

15. The system of claim 14, wherein the metal anode is on a side of the second substrate away from the cathode.

16. The system of claim 1, wherein the cathode comprises an array of carbon nanotubes.

17. The system of claim 1, further comprising:
   a second X-ray source comprising a plurality of X-ray generators configured to respectively emit a plurality of X-rays toward the object; and
   a second X-ray detector configured to detect images of the object formed respectively by the plurality of X-rays from the second X-ray source;
   wherein a combination of the first X-ray source and the first X-ray detector and a combination of the second X-ray source and the second X-ray detector have different orientations.

18. The system of claim 17, wherein the orientations are perpendicular to each other.

* * * * *